United States Patent
Ribier et al.

[11] Patent Number: 5,993,831
[45] Date of Patent: Nov. 30, 1999

[54] COMPOSITION PROVIDING A LASTING COSMETIC AND/OR PHARMACEUTICAL TREATMENT OF THE UPPER EPIDERMAL LAYERS BY TOPICAL APPLICATION ON THE SKIN

[75] Inventors: Alain Ribier, Paris; Pascal Richart, L'Hay-les-Roses; Rose-Marie Handjani, Paris, all of France

[73] Assignee: L'Oreal, Paris, France

[21] Appl. No.: 08/050,315

[22] PCT Filed: Aug. 27, 1992

[86] PCT No.: PCT/FR92/00824

§ 371 Date: May 18, 1993

§ 102(e) Date: May 18, 1993

[87] PCT Pub. No.: WO93/05753

PCT Pub. Date: Apr. 1, 1993

[30] Foreign Application Priority Data

Sep. 13, 1991 [FR] France .................................. 91 11344

[51] Int. Cl.⁶ ...................................................... A61K 7/48
[52] U.S. Cl. ...................... 424/401; 424/497; 424/78.03; 428/402.2; 428/402.21; 264/4.1; 264/4.6; 514/937; 514/938; 514/939

[58] Field of Search ...................................... 424/401, 497, 424/78.03; 514/937, 938, 939, 944; 428/402.2, 402.21; 264/4.1, 4.6

[56] References Cited

U.S. PATENT DOCUMENTS

| 3,965,033 | 6/1976 | Matsukawa et al. | 252/316 |
| 5,049,322 | 9/1991 | Divissagvet et al. | 264/4.1 |

FOREIGN PATENT DOCUMENTS

| 0254447 | 1/1988 | European Pat. Off. . |
| 0274961 | 7/1988 | European Pat. Off. . |
| 0409690 | 1/1991 | European Pat. Off. . |
| 2166651 | 5/1986 | United Kingdom . |

*Primary Examiner*—Jyothsna Venkat
*Attorney, Agent, or Firm*—Nixon & Vanderhye P.C.

[57] ABSTRACT

A composition containing, in a suitable carrier, nanoparticles of one or more nonbiodegradable polymer(s) encapsulating an oily phase which contains at least one active oil and/or at least one carrier oil and/or at least one active ingredient in an active oil and/or a carrier oil. At least one active ingredient is chosen from those with prolonged cosmetic and/or pharmaceutical activity. The nanocapsules have a size of 100–1000 nm.

7 Claims, No Drawings

COMPOSITION PROVIDING A LASTING COSMETIC AND/OR PHARMACEUTICAL TREATMENT OF THE UPPER EPIDERMAL LAYERS BY TOPICAL APPLICATION ON THE SKIN

This application is a 371 of PCT/FR92/00824 filed on Aug. 27, 1992.

The present invention relates to a composition providing a lasting cosmetic and/or pharmaceutical treatment of the upper epidermal layers by topical application on the skin.

The application to the skin of oils active per se and/or containing an active ingredient has long been known in the cosmetic and/or pharmaceutical fields. These oils can be used as they are; they are most often in the form of a water-in-oil or oil-in-water emulsion. They may also, in a known manner, be applied encapsulated in microcapsules of gelatin or of other polymers which are crushed on the skin so as to release the oils, these microcapsules being, in general, between $5 \times 10^4$ and $2 \times 10^6$ nanometres in size (see for example U.S. Pat. No. 4,976,961). But the oils applied remain for the most part at the surface of the skin where they can be rapidly removed simply by rubbing, for example, upon contact with clothing, or by washing.

Moreover, there are known, by the name of nanoparticles, colloidal particles which are much smaller in size than microparticles since their size is generally of the order of 10 to 1000 nm; in these nanoparticles, an active ingredient is trapped by encapsulation and/or by adsorption and/or absorption (see J. Keuter, J. microencapsulation 1988 Vol. 5, pages 115–127). The term nanoparticles is generic and covers, on the one hand, nanospheres and, on the other hand, nanocapsules; the term "nanospheres" designates nanoparticles consisting of a porous polymeric matrix on which the active ingredient is absorbed and/or adsorbed and the term "nanocapsules" designates the nanoparticles consisting of a polymeric membrane surrounding a core formed by the active ingredient. The polymers which can be used for the manufacture of nanocapsules may be, in a known manner, either biodegradable materials or nonbiodegradable materials.

In French Patent Application 90,034,418, the applicant described a cosmetic composition for topical application containing nanocapsules of biodegradable polymer encapsulating an oily phase which contains an active ingredient. The applicant has found that the nanocapsules penetrate into the skin and release their contents for the most part into the epidermis; the nanocapsules being of biodegradable polymer, they are rapidly degraded in the epidermis by the action of the enzymes present therein and release the oily phase which they contain. In this composition, the oily phase, being released in situ in the epidermis, can therefore no longer be removed simply by rubbing or by washing. The active ingredient has an immediate maximum effect, which is advantageous in many treatments where an immediate activity is desired, such as anti-inflammatory treatments.

But in a number of cosmetic and/or pharmaceutical treatments, it is desired that the active ingredients should have a prolonged action over time without the need for the application to be repeated too frequently. Such is the case for example for protecting the skin with sunscreen agents, for the direct coloring of the skin with colorants or pigments and for treating the skin with deodorants, humectants or free radical-capturing agents.

According to the present invention, it was found that a composition containing nanocapsules could be obtained, in which composition the active ingredients have a prolonged action over time, using nanocapsules of a nonbiodegradable polymer.

The subject of the present invention is therefore a composition providing a cosmetic and/or pharmaceutical treatment of the upper epidermal layers by topical application to the skin, each application preferably needing to have a prolonged effect over time, characterised by the fact that it comprises, in a suitable carrier, nanocapsules of nonbiodegradable polymer(s) encapsulating an oily phase containing at least one active oil and/or at least one active ingredient in an active oil, the nanocapsules being between 100 and 1000 nm, preferably between 200 and 800 nm, in size.

At least one of the active ingredients is preferably chosen from those which need to have a lasting cosmetic and/or pharmaceutical action on the skin. "Lasting action" is understood to mean an activity lasting at least one hour.

It was observed that the nanocapsules between 100 and 1000 nm in size are sufficiently small to be able to slip between the outermost corneocytes of the stratum corneum without however reaching the living epidermis. The nanocapsules therefore penetrate into the first, poorly linked, strata of the stratum corneum and thus escape the risks of being rapidly removed from the surface of the skin simply by rubbing. They will be naturally removed with the normal desquamation of the skin.

The weight of the nanocapsules, charged with an oily phase, which are used advantageously constitutes 0.1 to 20% of the total weight of the composition, and preferably 0.5 to 10% by weight.

Nonbiodegradable polymers are understood to mean, in the present patent application, the polymers forming nanocapsule membranes which are not degraded by the enzymes of the skin. These membranes, according to the choice of the polymer, may be semipermeable.

The nanocapsule membranes according to the invention must also be very resistant to their surrounding medium after formulation of the composition, whether this surrounding medium is aqueous or oily.

Among the polymers having the above characteristics, there may be mentioned:

vinyl chloride and vinyl acetate copolymers, for example those marketed under the name "RHODOPAS AX 8515" by the company RHONE POULENC;

methacrylic acid and methacrylic acid methyl ester copolymers, for example those marketed under the name "EUDRAGIT L 100" by the company ROHM PHARMA;

polyvinyl acetophthalate;

cellulose acetophthalate;

crosslinked polyvinylpyrrolidone-vinyl acetate copolymer;

polyethylene vinyl acetates;

styrene alkyl alcohol oligomers;

methacrylic acid and ester copolymers polyacrylonitriles;

polyacrylamides;

polyethylene glycols;

poly(hydroxyethyl methacrylate);

cellulose derivatives;

polyamides;

polyethylenes;

polypropylene;

organopolysiloxanes including polydimethylsiloxanes;

gelatin.

The nanocapsules obtained generally have a transparent membrane. Under these conditions, it was observed that the direct colorants for the skin and the sunscreen agents can respectively act as coloring or protecting agent for the skin without being released from the nanocapsules. It was observed that in spite of a discontinuous distribution of the sunscreen agent or of the colorant, a continuous effect was obtained, that is to say a uniform protection or coloring of the skin.

Insofar as the membrane is semipermeable, it permits exchanges of water or moisture with its surrounding medium. Consequently, if the nanocapsules contain a humectant as active ingredient, the latter will be able to fulfil its function and to moisturize the skin.

Given that the membrane may be semipermeable under the action of the sebum, bactericidal agents, deodorants and antiseborrhoeic agents may be encapsulated in the nanocapsules. They will be released over time under the action of the sebum.

The oily phase encapsulated in the nanocapsules may contain an active oil. This oil may be especially an agent for screening out UV-A and/or UV-B, for example based on ethylhexyl p-methoxycinnamate (sold under the name "PARSOL MCX") or 4-tert-butyl-4'-methoxydibenzoylmethane (sold under the name "PARSOL 1789"), and/or a bactericidal and/or fungicidal essential oil such as thyme oil, an oil with humectant activity such as pentaerythritol tetra(2-ethylhexanoate) and an oil with anti-free radical activity such as alpha-tocopherol.

The nonactive carrier oils are preferably chosen from simple triglycerides or triglycerides modified in particular by oxyethylenation, volatile silicone oils and mineral oils.

The active ingredient is preferably an oleophilic active ingredient which dissolves in oil. But it may also be in the form of a dispersion, suspension or emulsion.

It is possible, according to the invention, to introduce into the oily phase at least one nonoily active ingredient in a carrier oil and/or in an active oil. This active ingredient, irrespective of its presentation, may be a humectant such as hyaluronic acid, orotic acid or a lipoprotein, an anti-acne agent, a lipid regulator such as an extract of Centella asiatica or gamma-orizanol, anti-aging agent such as vitamin A palmitate, a colorant, a pigment, an emollient such as an isopropyl ester, a keratolytic agent such as retinoic acid or 5-n-octanoylsalicylic acid.

According to the invention, the composition may also contain nanocapsules of biodegradable polymer(s) encapsulating an oily phase containing at least one active ingredient which preferably has an immediate action after application. A composition may thus be obtained containing both (an) active ingredient(s) with immediate action and (an) active ingredient(s) with prolonged action.

The compositions according to the invention may be provided in the form of a serum, a lotion, an aqueous, dilute alcoholic or oily gel, a water-in-oil or oil-in-water emulsion, aqueous dispersions of lipid vesicles consisting of ionic or nonionic lipids or a mixture of both (mixed vesicles); it being possible for these vesicular dispersions, in addition, to contain where appropriate a dispersed oil according to the teaching of FR-A 2,485,921.

The composition may also contain pharmaceutically and/or cosmetically acceptable adjuvants which form the carrier of the composition after formulation. Of these adjuvants there may be mentioned fatty substances, oils, vaseline, preservatives, thickening agents, colorants and perfumes.

The nanocapsules according to the invention are preferably prepared in a known manner by the preformed polymer precipitation process of H. Fessi and JP. Devissaguet described in EP-A 0,274,961.

In this case, the nanocapsules are obtained by precipitation of the polymer around a dispersion of oily droplets by injecting into an aqueous phase, which may contain one (or more) surface-active agent(s), a mixture consisting of the oil(s) to be encapsulated, at least one polymer and at least one solvent, and then by evaporating the solvent. If desired, all or part of the solvent is removed so as to obtain a colloidal suspension of a given concentration of nanocapsules or to obtain, after addition of stabilizing substances, a powder of nanocapsules.

Other known processes for manufacturing nanocapsules may also be used.

The examples given below, solely by way of illustration with no limitation being implied, will make it possible to understand the invention more clearly.

EXAMPLES 1 to 5

Preparation of Nanocapsules

In a 100-ml beaker, 125 mg of condensate of ethylene oxide and propylene oxide in a weight ratio of 20/80, with a mean molecular weight of 1750 and 8350 respectively, marketed under the name "PLURONIC F 68" by the company BASF, are dissolved in 50 ml of demineralized water, with stirring by means of a magnetic bar revolving at 400 rpm.

Into this aqueous phaser thermostated at 40° C., are poured slowly 25 ml of absolute alcohol in which the nonbiodegradable polymer and the active ingredient (or the active ingredients) used in the example considered have previously been dissolved at a temperature of 40° C.

The stirring is maintained for 20 minutes at a temperature of 40° C. and then the mixture is allowed to return to room temperature.

The dispersion of nanocapsules obtained is then transferred to a 250-ml round-bottomed flask which is connected to a rotary evaporator and the alcohol and a portion of the water are evaporated until 10 ml of a white free-flowing colloidal dispersion of nanocapsules are obtained. The mean diameter and the polydispersity (PI) are measured with a "nanosizer" (Coultronics granulometer).

The PI value is evaluated on a scale from 0 to 9, 0 corresponding to a nearly perfect homogeneity of the particle size and 9 indicating a high ratio between the size of the largest particles and that of the smallest particles. The polymers and the active ingredients used as well as the mean diameter and the polydispersity of the nanocapsules obtained are given in Table I below.

TABLE I

| Example | Polymer | Active ingredient | Mean diameter in nm | Polydispersity |
| --- | --- | --- | --- | --- |
| 1 | 125 mg of methacrylic acid and methacrylic acid methyl ester | –500 mg of solar UV-B-screening agent marketed under the name | 600 | 2 |

TABLE I-continued

| Example | Polymer | Active ingredient | Mean diameter in nm | Polydispersity |
|---|---|---|---|---|
| | copolymer marketed under the name "EUDRAGIT L 100" by the company ROHM PHARMA. | "PARSOL MCX" by the company GIVAUDAN | | |
| 2 | AS ABOVE | –100 mg of solar UV-A-screening agent marketed under the name "PARSOL 1789" by the company "GIVAUDAN" –400 mg of alpha-tocopherol marketed by the company ROCHE | 310 | 2 |
| 3 | AS ABOVE | –100 mg of solar UV-A-screening agent marketed under the name "PARSOL 1789" –400 mg of solar UV-B-screening agent "PARSOL MCX" marketed by the company GIVAUDAN | 670 | 2 |
| 4 | AS ABOVE | –500 mg of solar UV-B-screening agent marketed under the name "ESCALOL 507" by the company MALLINCKRODT. | 550 | 2 |
| 5* | 125 mg of vinyl chloride and vinyl acetate copolymer marketed under the name "RHODOPAS AX 8515" by the company RHONE POULENC. | –500 mg of alpha-tocopherol marketed by the company ROCHE. | 200 | 1 |

*In this Example, the alcohol is replaced with acetone and all the temperatures are adjusted to 20° C.

EXAMPLE 6 (COMPARATIVE)

The protection index provided by two compositions, composition A containing a sunscreen agent and composition B according to the invention containing the same sunscreen agent encapsulated in nanocapsules, was compared.

a) Formulations

Composition A

Solar UV-B-screening agent marketed under the name "PARSOL MCX" by the company GIVAUDAN . . . 4 g Mixture of cetyl stearyl and oxyethylenated ethylenated cetyl stearyl alcohols containing 33 moles of ethylene oxide (80/20 by weight) . . . 2.8 g Glycerol mono- and distearate . . . 0.8 g (40/50 by weight)

Cetyl alcohol . . . 0.6 g

Polydimethylsiloxane . . . 0.6 g

Vaseline oil . . . 6 g

Butyl para-hydroxybenzoate . . . 0.08 g

Demineralized water qs . . . 100 g

Composition B

Dispersion of nanocapsules prepared according to Example 1 . . . 80 g

Mixture of cetyl stearyl and oxyethylenated cetyl stearyl alcohols containing 33 moles of ethylene oxide (80/20 by weight) . . . 2.8 g Glycerol mono- and distearate (40/50 by weight) . . . 0.8 g Cetyl alcohol . . . 0.6 g Polydimethylsiloxane . . . 0.6 g Vaseline oil . . . 6 g Butyl para-hydroxybenzoate . . . 0.08 g Demineralized water qs . . . 100 g b) Trials The two compositions were regularly applied to the back of ten subjects in an amount of 2 mg/cm$^2$.

The skin is then subjected to UV-B radiation 15 to 20 min after application of the compositions.

An opaque plate provided with circular openings 15 mm in diameter is placed over the area to be exposed. These openings are closed one after the other at defined intervals so as to have areas of the skin which have received different doses of radiation.

The observations are carried out (24±2) hours after exposure to radiation. The first cycle just visible but clearly delimited is determined and the dose of UV-B energy received (MED) is determined.

The protection index is the ratio of the MED in the presence of the test product and the MED in the absence of the anti-sun product.

The results obtained with the test compositions are as follows:

| Composition | Protection index |
|---|---|
| A | 3.85 |
| B | 5.30 |

These results demonstrate that the composition according to the invention results in a significant increase in the protection index for the same concentration of sunscreen agent.

We claim:

1. A composition for the treatment of the upper epidermal layers of the skin, said composition comprising, in a carrier suitable for topical application to the skin, nanocapsules of a nonbiodegradable polymer encapsulating an oily phase,
    said oily phase, encapsulated in said nanocapsules of said nonbiodegradable polymer, containing an effective active oil or an oil having anti-free radical activity,
    said nanocapsules of said nonbiodegradable polymer having a size ranging from 100 to 1,000 nm and being present in an amount ranging from 0.1 to 20 percent by weight based on the total weight of said composition.

2. The composition of claim 1 wherein said nanocapsules of said nonbiodegradable polymer have a size ranging from 200 to 800 nm.

3. The composition of claim 1 wherein said nanocapsules of said nonbiodegradable polymer are present in an amount ranging from 0.5 to 10 percent by weight based on the total weight of said composition.

4. The composition of claim 1 wherein said nonbiodegradable polymer is selected from the group consisting of a vinyl chloride-vinylacetate copolymer and a methacrylic acid-methacrylic acid methyl ester copolymer.

5. A composition for the treatment of the upper epidermal layers of the skin, said composition comprising, in a carrier suitable for topical application to the skin, nanocapsules of a nonbiodegradable polymer encapsulating an oily phase, said oily phase encapsulated in said nanocapsules of said nonbiodegradable polymer, containing an active oil to screen out solar UV-A rays and solar UV-B rays, said nanocapsules of said nonbiodegradable polymer having a size ranging from 100 to 1,000 nm and being present in an amount ranging from 0.1 to 20 percent by weight based on the total weight of said composition.

6. A composition for the treatment of the upper epidermal layers of the skin, said composition comprising, in a carrier suitable for topical application to the skin, nanocapsules of a nonbiodegradable polymer encapsulating an oily phase, said oily phase encapsulated in said nanocapsules of said nonbiodegradable polymer, containing an active oil having an anti-free radical activity, said nanocapsules of said nonbiodegradable polymer having a size ranging from 100 to 1,000 nm and being present in an amount ranging from 0.1 to 20 percent by weight based on the total weight of said composition.

7. A composition for the treatment of the upper epidermal layers of the skin, said composition comprising, in a carrier suitable for topical application to the skin, nanocapsules of a nonbiodegradable polymer encapsulating an oily phase, said oily phase encapsulated in said nanocapsules of said nonbiodegradable polymer containing $\alpha$-tocopherol, said nanocapsules of said nonbiodegradable polymer having a size ranging from 100 to 1,000 nm and being present in an amount ranging from 0.1 to 20 percent by weight based on the total weight of said composition.

* * * * *